United States Patent [19]

Mayeux

[11] Patent Number: 5,305,788

[45] Date of Patent: Apr. 26, 1994

[54] STREAM SELECTOR FOR PROCESS ANALYZER

[75] Inventor: Donald P. Mayeux, Prairieville, La.

[73] Assignee: Whitey Co., Highland Hts., Ohio

[21] Appl. No.: 928,780

[22] Filed: Aug. 13, 1992

[51] Int. Cl.$^5$ ............................................. F16K 24/00
[52] U.S. Cl. .................................. 137/583; 251/330; 137/614.11
[58] Field of Search ........... 73/864.81, 864.83, 863.86; 137/312, 614.11, 614.18, 869, 628, 583; 251/305-308, 330

[56] References Cited

U.S. PATENT DOCUMENTS

| | | | |
|---|---|---|---|
| 2,473,465 | 6/1949 | Betz | 137/614.11 |
| 3,314,448 | 4/1967 | Wolff et al. | 137/628 |
| 3,509,913 | 5/1970 | Lewis | 137/614.11 |
| 4,687,017 | 8/1987 | Danko et al. | 137/312 |
| 4,846,212 | 7/1989 | Scobie et al. | 137/312 |
| 5,000,212 | 3/1991 | Tervo | 251/283 |
| 5,170,659 | 12/1992 | Kemp | 137/312 |

Primary Examiner—Robert Raevis
Attorney, Agent, or Firm—Fay, Sharpe, Beall, Fagan, Minnich & McKee

[57] ABSTRACT

A stream selector for a process analyzer. The stream selector includes a valve module having two block valves and a bleed valve. In a first mode, the block valves are closed and the bleed valve is open. In a second mode, the block valves are open and the bleed valve is closed. In a third mode, all of the valves are open, thus ensuring that the module is completely purged. A stream-selection valve manifold is made by joining two or more valve modules side by side to form a common outlet and a common passageway, thus ensuring that the manifold is completely purged. The stream selector also provides a single block-and-bleed valve module having a disposal passageway which establishes fluid communication between a vent compartment and an external area suitable for the safe disposal of sample fluids and compressed gas contained in the valve module. The flat-face sealing structure of each valve is very tolerant of scratching and/or irregularities in the sealing structure and of abrasive particulates which may be present in the sample fluid, even to minor structural damage to the sealing structure.

18 Claims, 7 Drawing Sheets

STREAM SELECTOR FOR PROCESS ANALYZER

BACKGROUND OF THE INVENTION

The present invention relates to stream selection. More particularly, the present invention relates to the selection of sample streams being routed to a process analyzer.

It is common practice to utilize a single automated process analyzer for analyzing multiple sample streams. This significantly reduces the cost of analyzing gas and liquid process streams in petrochemical plants, refineries and other process-related industries. The sample streams are generally transported near to an analyzer by tubing or piping. An automated valving manifold, usually electronically controlled, sequentially selects and diverts individual sample streams to the automated analyzer. This type of valving arrangement is generally referred to as a "stream-select manifold."

It is extremely important that sample-stream cross-contamination does not occur; i.e., absence of contamination of one sample stream by another in the sample stream selected for analysis. The most likely source of cross-contamination is from leaking "stream-select valves" in the stream-selection valving manifold.

Another common problem is the contamination of a stream selected for analysis by residual fluid from a previous sample stream. This is likely to occur in a common passageway between the valve manifold and the analyzer. Valve-manifold designs have either "dead volume," irregular passageways, or large internal volumes, which require longer period of sample flow purging) before all residual fluid from a previously selected sample stream is removed. A common source of "difficult-to-purge" internal valve manifold volume is pipe fittings which provide an irregular internal surface. A common source of dead volume is the space between the block valve of a "non-selected" stream and the common sample fluid passage to an analyzer.

When longer sample-stream purge periods are required, it reduces the number of analyses which can be performed by an analyzer in a given period of time. This can increase the cost for analysis by requiring additional analyzers or otherwise negatively impact process adjustments based on current analysis.

Most important, however, is the increased volume of purged sample material which must be discarded. This also increases cost and presents a greater risk of contaminating the environment.

Valves utilized in stream-select manifolds for the most part were designed for ordinary pneumatic and hydraulic fluid-handling applications. Designs have been altered to some degree to accommodate stream-select manifold requirements. But few are designed exclusively for that purpose. Those which are designed primarily for stream selection are of the single block valve design, and are therefore prone to cross-contamination problems when even a slight leak develops.

Modular valve manifold arrangements are well known and in common service. These manifolds, however, are designed to facilitate the addition or removal of individual valves, and to reduce the number of tube and/or pipe fittings required. Their main purpose is to reduce space in pneumatic and hydraulic, not analytical, applications. Hence little consideration has been given to reducing internal volume and/or "dead" (unpurged) space, or the prevention of cross-contamination by residual fluids. Few if any provide double-block-and-bleed (DBB) protection from cross-contamination. Some manifold valve designs even allow stacking of manifold modules to create a manifold of a desired length; however, the valves are a separate entity, and are attached to the manifold.

Another common problem with stream-selection valves is "fugitive emission" of sample fluids. This typically occurs when a valve stem seal fails. A metal bellows or diaphragm is frequently employed to seal the external actuation linkage to a valve's internal sealing mechanism. This arrangement, particularly when used in combination with a secondary packing, is very effective in reducing fugitive emission from valves. However, embrittlement of metal bellows or diaphragms, particularly in hydrogen-rich sample-stream service, and fatigue from repeated actuation, often causes premature stem-seal failures. Additionally, valves employing the bellows/diaphragm seal design are expensive, thus limiting their application. Furthermore, when the bellows or diaphragm fails, there can be an abrupt release of potentially flammable and/or toxic fluids to the surrounding environment. In summary, bellows/diaphragm valve stem seals are very effective during their normal service life, but have a severe and potentially unsafe failure mode.

Pneumatic actuation is often preferred in lieu of electric actuation for valves used in hazardous or electrically-classified environments. Current valve designs generally employ discrete pneumatic actuators usually mounted external to the valve with mechanical linkage through a seal to the internal valving mechanism. This arrangement results in a bulky design which takes up large amounts of valuable panel space. This is a particularly important consideration when considering the cost of providing panel space in a typical analyzer housing or environment. The large bulk also precludes close coupling of valves to minimize internal valve-manifold volume.

These and other problems encountered by the prior art are solved, eliminated, or minimized by the present invention.

SUMMARY OF THE INVENTION

In general, the present invention in one aspect provides a valve module for a process analyzer. The module comprises a first block valve having a first opening, a second block valve having a second opening, and a bleed valve having a third opening. The first and second block valves are so constructed and arranged that both are closed simultaneously or both are open simultaneously. The block valves and the bleed valve are so constructed and arranged that, in a first mode, the block valves are closed and the bleed valve is open; in a second mode the block valves are open and the bleed valve is closed; and in a third mode, all of the valves are open, thereby ensuring that the module is completely purged.

The valve module further comprises flat-face sealing means for closing the valves by pressing the sealing means against a flat sealing surface in a linear motion, and for opening the valves by breaking contact between the sealing means and the flat sealing surface.

In a second aspect the present invention provides a stream-selection valve manifold. The valve manifold comprises first and second valve modules joined side by side to form a common outlet passageway and a common vent passageway. Each valve module includes two block valves and a bleed valve. The block valves are so constructed and arranged that both are closed simultaneously or both are open simultaneously. The three valves are so constructed and arranged that, in a first mode, the block valves are closed and the bleed valve is open; in a second mode, the block valves are open and the bleed valve is closed; and in a third mode, all three valves are open, thereby ensuring that the module is completely purged.

Each valve module further comprises flat-face sealing means for closing the valves by pressing the sealing means against a flat sealing surface, and for opening the valves by breaking contact between the sealing means and the flat sealing surface. One of the block valves communicates with an inlet passageway. The other block valve communicates with an outlet passageway. The bleed valve communicates with a vent passageway. Flow-through means hold the first and second valve modules in a fixed configuration wherein the outlet passageways of the first and second valve modules are aligned to form a common outlet passageway to and through the flow-through holding means, and the vent passageways from the first and second valve modules are aligned to form a common vent passageway, thereby ensuring that the manifold is completely purged.

In a third aspect, the invention provides a single block-and-bleed valve module. The module comprises a block valve, a sample-fluid compartment, a vent compartment, an internal pneumatic actuator, a sample-inlet first passageway, a sample-outlet second passageway, third and fourth passageways, first biasing means for closing the block valve, second biasing means for opening the valve, and a body having a cavity therein for housing the block valve, the sample-fluid compartment, the vent compartment, the pneumatic actuator, and the first, second, third, and fourth passageways.

The internal pneumatic actuator includes an actuator piston and an actuator compartment. The actuator compartment is constructed and arranged to receive compressed gas from an external source.

The first biasing means close the block valve by urging the piston in a first direction. The second biasing means, which include a compressed gas, open the valve by urging the piston in a second direction.

The block valve is so constructed and arranged that, when closed, fluid communication is blocked between the inlet passageway and the sample-fluid compartment; when open, the inlet passageway, the sample-fluid compartment, and the outlet passageway are in fluid communication.

The inlet passageway provides means for fluid communication from the external environment to the sample-fluid compartment. The outlet passageway provides means for fluid communication from the sample-fluid compartment to the external environment. The third passageway provides means for introducing a compressed gas into the actuator compartment. The fourth passageway provides means for fluid communication between the vent compartment and an external area suitable for the safe disposal of fluids contained within the valve module. The pressure within the vent compartment and the fourth passageway is normally maintained at a level equal to or lower than that of the sample-fluid compartment, the sample-inlet passageway, the sample-outlet passageway, and the actuator compartment, in order to prevent fugitive emission of the sample fluid or of the compressed gas from the module into unprotected areas of the external environment.

DETAILED DESCRIPTION OF THE INVENTION

The present invention, in a first embodiment (FIG. 3), provides a valve module 33 for a process analyzer. The module 33 comprises an internal pneumatic actuator, an inlet block valve 33b, an outlet block valve 33c, and a bleed valve 33d. The two block valves 33b, 33c are constructed and arranged so that both are closed or both are open simultaneously. The bleed valve 33d is constructed and arranged so that when the block valves 33b, 33c are open, the bleed valve 33d is closed: when the block valves 33b, 33c are closed, the bleed valve 33d is open. The three valves 33b, 33c, 33d are contained and disposed in and by a body 16 having an inlet port 19, an outlet port 18a, and a vent port 17 for the inlet valve 33b, outlet valve 33c, and valve 33d, respectively (FIGS. 7-10).

Figure 7:
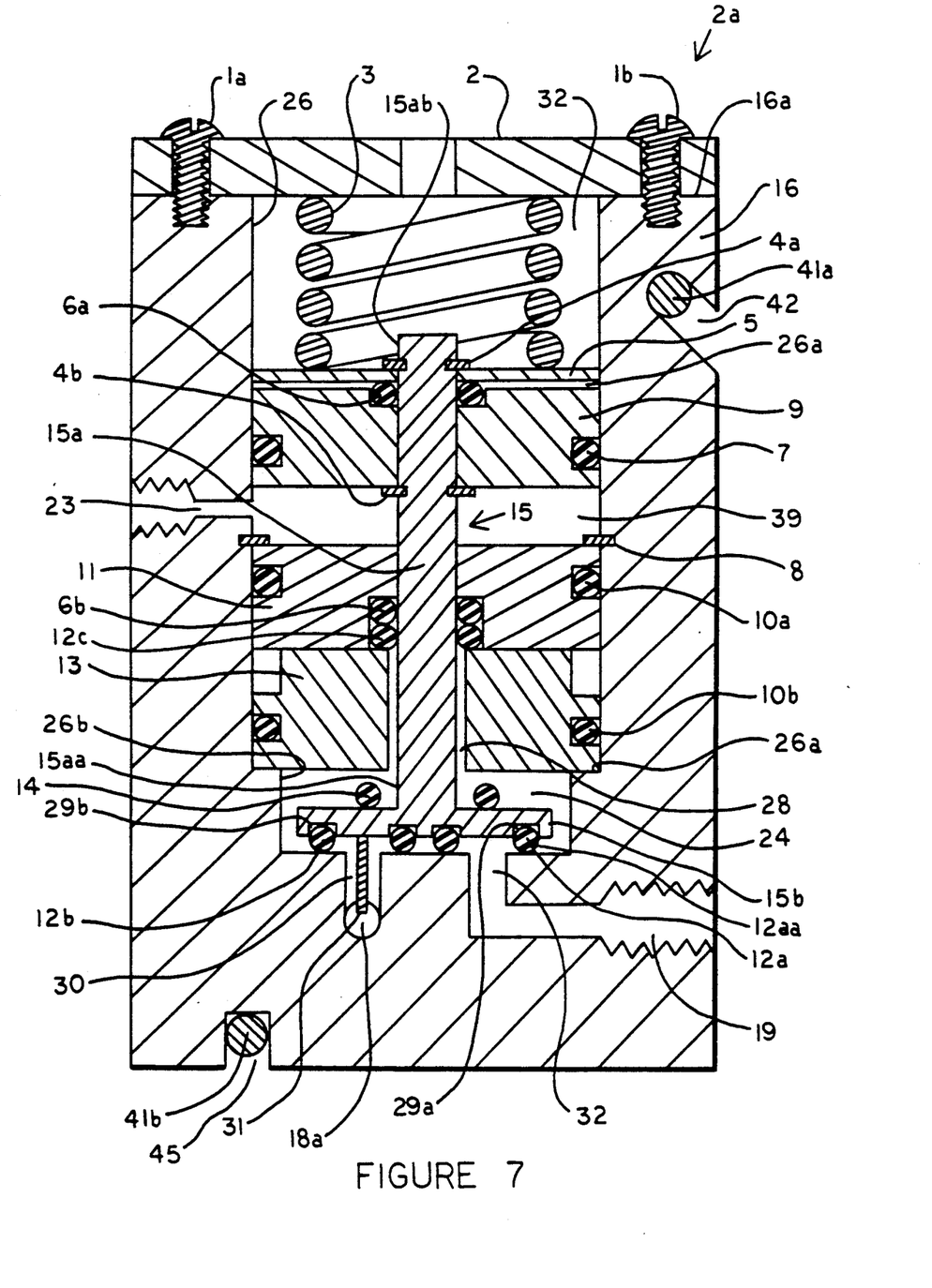
FIG. 7 is a cross-sectional view of the valve manifold shown in FIG. 4, taken along the cutting line 7—7.
Figure 9:
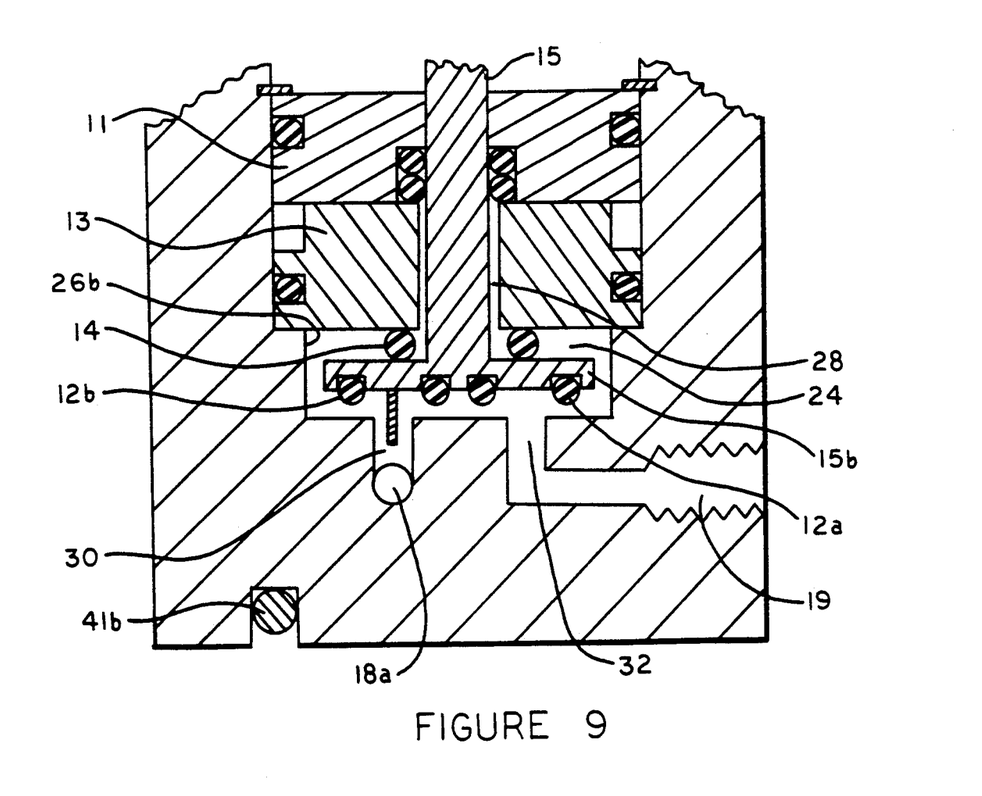
FIGS. 9 and 10 are portions of the cross-sectional view of the Valve manifold shown in FIG. 7.
Figure 10:
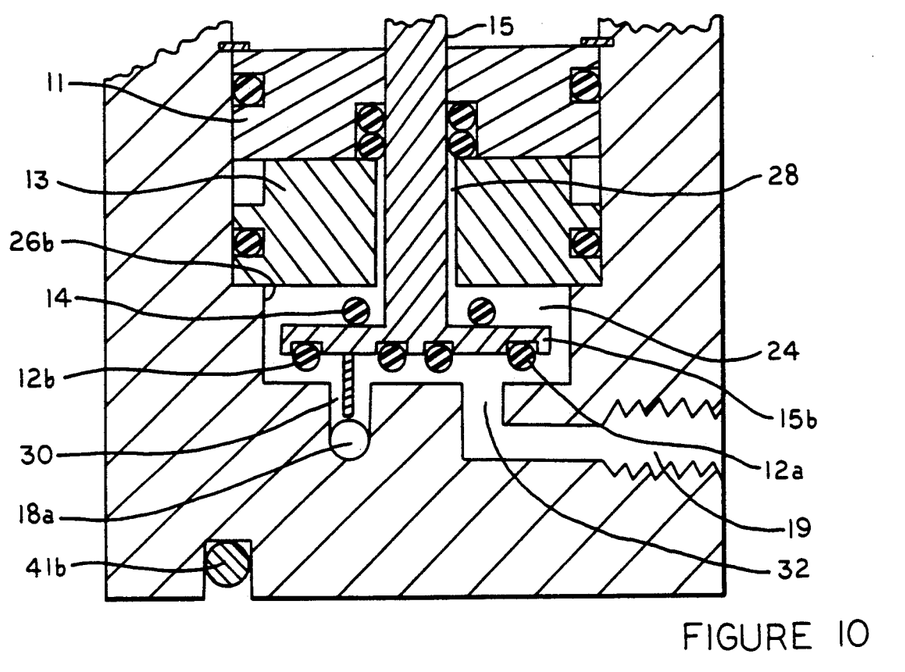

The valve module 33 comprises a valve poppet 15 having a stem 15a and a flange 15b, first biasing means 3 to urge the poppet 15 downward, and second biasing means to force the poppet 15 upward (FIGS. 7, 9, and 10). The first biasing means 3 may be a spring 3, a compressed gas, or other means. Preferably, however, the first biasing means is a spring 3 housed in a chamber 32. The second biasing means is preferably a compressed gas; it is stronger than the first biasing means 3, and prevails when the two are in opposition.

The three valves 33b, 33c, 33d and the pneumatic actuator are disposed within a cavity 26 in the body 16. (FIG. 7.)

When the poppet 15 is in its extreme lower position (FIG. 7), in response to the first biasing means 3 and in the absence of the second biasing means, the sample inlet and outlet valves 33b, 33c are in a closed or blocked configuration, and the bleed valve 33d is open. When the poppet 15 is in its extreme upper position (FIG. 9), in response to the second biasing means, the inlet and outlet valves 33b, 33c are open, and the bleed valve 33d is closed. During transition between these two extreme positions, which is momentary, all three valves 33b, 33c, 33d are open (FIG. 10).

It will be understood that the portion of the cavity 26 providing the second biasing means may be maintained at a pressure substantially above atmospheric, even "in the absence of the second biasing means." Such a condition may indeed be beneficial, in order to prevent fugitive fluid emission from the modular body 16. It is therefore necessary, as stated above, that the second biasing means be understood and is herein defined as a pressure sufficient to overcome the first biasing means.

Preferably, the valves 33b, 33c, and 33d comprise flat-face sealing means. Even more preferably, the valves 33b, 33c, and 33d include O-rings (FIGS. 7, 9, and 10).

Figure 8:
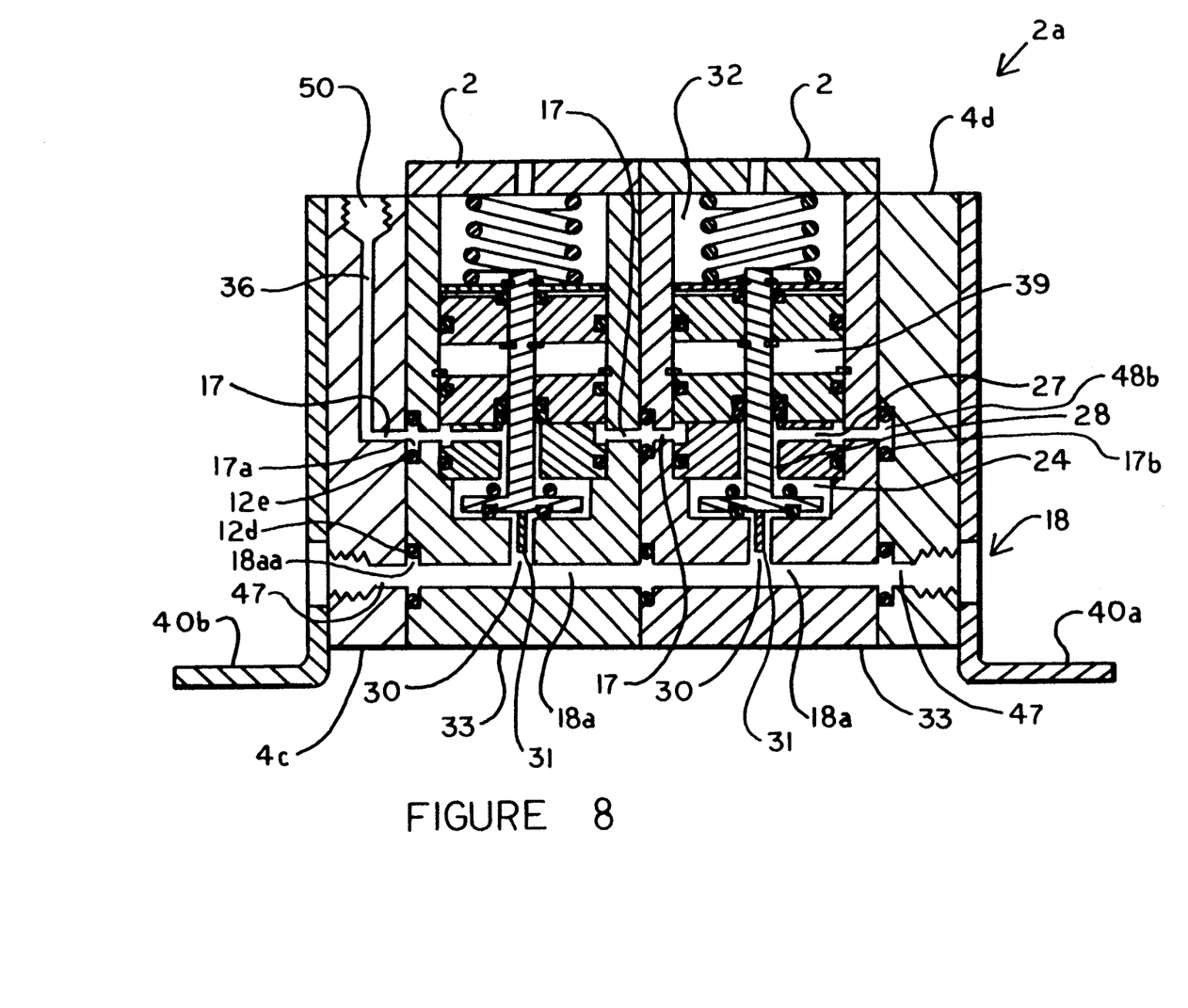
FIG. 8 is a cross-sectional view of the valve manifold shown in FIG. 4, taken along the cutting line 8—8.
Figure 12:
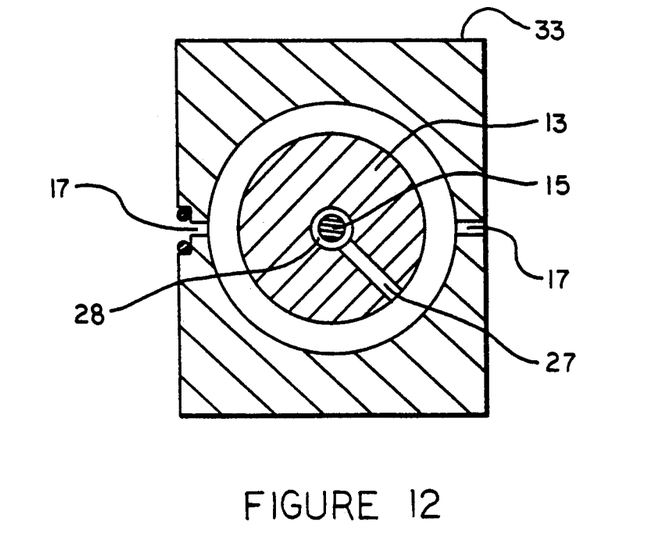
FIG. 12 is a cross-sectional view of the manifold shown in FIG. 4, taken along the cutting line 12—12.

More specifically, a seal-plug bottom part 13 is positioned on a shoulder 26a formed by a reduction of cross-sectional area at the lower end 26b of the cavity 26. (FIGS. 7, 9 and 10 ) An O-ring 10b seals the outer surface of the seal-plug bottom part 13 to the inner surface of the cavity 26. A seal-plug top part 11 is disposed over the seal-plug bottom part 13. An O-ring 10a seals the outer surface of the seal-plug top part 11 to the inner surface of the cavity 26. A snap ring 8 retains the seal-plug top part 11 and seal-plug bottom part 13 in a fixed position. The poppet 15, comprising a stem 15a and flange 15b, extends axially within the cavity 26. Grooves 29a and 29b in the lower surface of the poppet 15 retain O-rings 12a and 12b. An alignment pin 31 disposed in a passageway 30 maintains axial alignment of the O-ring 12a with a passageway 32 and of O-ring 12b with the passageway 30. A portion 12aa of the O-ring 12a which extends beyond its retaining groove 29a, when forced against the lower surface of a first compartment 24 and in axial alignment with the passageway 32, forms the sample inlet valve 33b which either blocks or permits fluid communication between a sample inlet passageway 19, the passageway 32, and the first compartment 24. In a similar manner, the O-ring 12b forms the sample outlet valve 33c which blocks or permits fluid communication between the outlet passageway 18a, the passageway 30, and the first compartment 24. An O-ring 14 axially disposed around the lower end 15aa of the poppet stem 15a, the upper surface of the poppet flange 15b, and the lower surface of the seal-plug bottom part 13 forms the bleed valve 33d which blocks or permits fluid communication between the first compartment 24 and passageways 28, 27, and 17. (FIGS. 7, 8, and 12.)

The width of the grooves 29a and 29b is from about seventy-five to about ninety-five percent of the width of the O-rings 12a and 12b, respectively. Preferably, the width of the grooves 29a and 29b is from about eighty to about ninety percent of the width of the O-rings 12a and 12b, respectively. Even more preferably, the O-rings 12a and 12b are made of an elastomer having a hardness of from about sixty-five to about seventy-five durometer units, as measured on a Shore "A" gauge, and the depth of the grooves 29a and 29b is from about eighty-seven to about ninety-one percent of the width of the O-rings 12 and 12b, respectively.

The valve poppet 15 is normally maintained in the extreme lower position (FIG. 7 by the downward force of the compression return spring 3 applied to the poppet stem 15a via an actuator washer 5, actuator piston 9, and an E-ring 4b.

A second compartment 39 comprises the middle portion of the cavity 26. The second compartment 39 is formed by the upper flat surface of the seal-plug top part 11 and the lower flat surface of the piston 9. When the second compartment 39 is pressurized by an external pneumatic source (not shown) of sufficient pressure via a passageway 23, an upward force resulting from the pneumatic pressure applied to the lower surface of the piston 9 overcomes the downward force applied by the compression return spring 3, and lifts the poppet 15 to its extreme upper position (FIG. 9). The poppet 15 is in the intermediate position shown in FIG. 10 for only a very short period of time while in transit between the two extreme positions.

O-rings 6b and 12c provide a dynamic seal between the plug-seal top part 11 and the poppet stem 15a, thereby ensuring fluid isolation at any position of the stem 15a between the passageway 28 and the second compartment 39.

The piston 9 and washer 5 are axially disposed and retained on the upper portion 15ab of the poppet 15 by E-rings 4a and 4b. The O-ring 6a, retained by the washer 5 and axially disposed in a third compartment 26a formed by the upper surface of the piston 9 and the lower surface of the washer 5, provides fluid isolation between the second compartment 39 and a fourth compartment 32, in which the spring 3 is disposed, and which is referenced to (equilibrated with) the atmosphere. The fourth compartment 32 is formed by the lower surface of a cover 2 and the upper surface of the washer 5. An O-ring 7 provides a dynamic seal between the piston 9 and the inside wall of the cavity 26. The cover 2, held to the top 16a of the body 16 by screws 1a and 1b, retains compression spring 3 (FIG. 7).

In a second embodiment (FIGS. 3, 4 and 8), the present invention provides a stream-selection valve manifold 2a for a process analyzer. The manifold 2a comprises: (a) a plurality of pneumatic valve modules 33 joined side-by-side, (b) first and second end plates 4c and 4d, and (c) first and second mounting brackets 40a and 40b. The passageway 18a in each valve module 33 is in alignment with the passageways 18a of adjacent valve modules 33 in the manifold 2a. The first and second end plates 4c and 4d, which are in fluid communication with the passageways 18a of adjacent modules 33, provide means for external fluid communication to a single common passageway 18 formed by the outlet passageways 18a of the individual modules 33.

Figure 3:
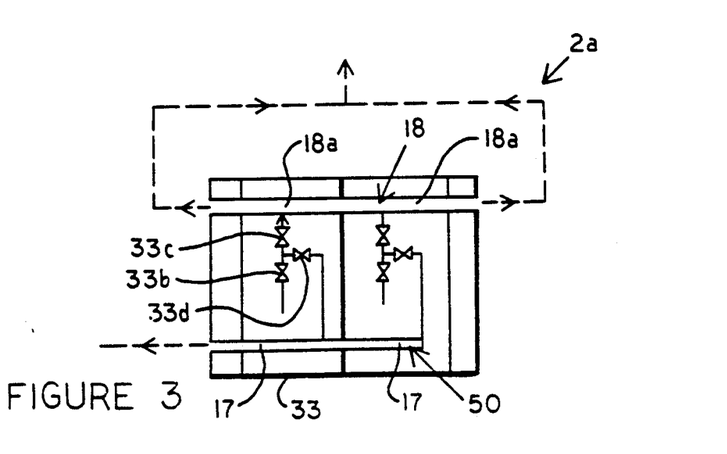
FIG. 3 is a schematic representation of a first embodiment of a stream-selection valve manifold for a process analyzer, made in accordance with the principles of the present invention.

An O-ring 12d (FIG. 8) in a gland 18aa at the end of each module's 33 passageway 18a provides a fluid seal with the passageway 18a of adjacent modules 33 and/or the end plates 4c, 4d. The passageways 17 in the valve modules 33 are joined and sealed with an O-ring 12e in a gland 17a to form a common vent passageway 36 which terminates as a threaded opening 50 in the end plate 4c. The passageway 17 is closed at the end plate 4d by an O-ring 17b in a gland 48b (FIGS. 3 and 8).

Figure 4:
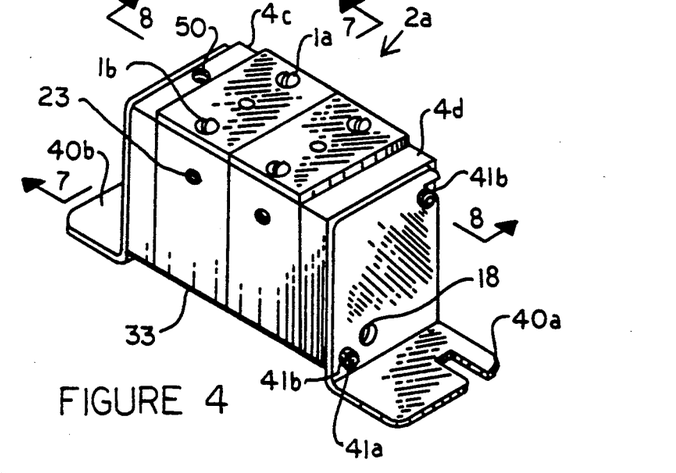
FIG. 4 is an isometric view of the stream-selection valve manifold shown schematically in FIG. 3.
Figure 11:
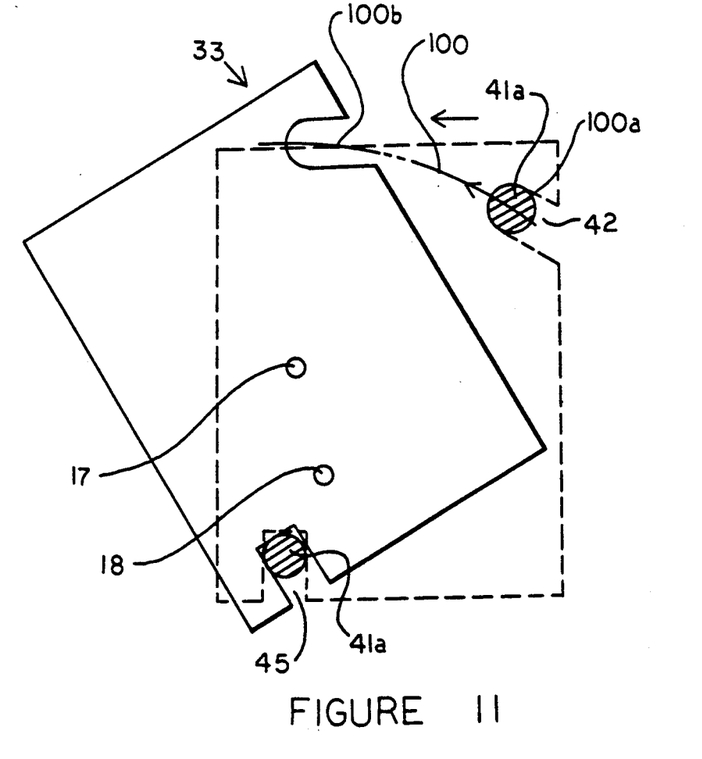
FIG. 11 is a schematic representation showing the removal of a valve module from the stream-selection valve manifold shown in FIGS. 3 and 4.

Mounting is facilitated by the use of mounting brackets 40a and 40b (FIGS. 4 and 8). The entire manifold 2a is held together by threaded rods 41a and nuts 41b. By loosening a first nut 41b at one end of a first threaded rod 41a, a valve module 33 can be removed by rotating it along a path 100 from a first point 100a to a second point 100b about the first threaded rod 41a disposed in a first slot 45. (FIG. 11.) After the valve module 33 has been rotated sufficiently (100b) to clear a second slot 42 from a second threaded rod 41a disposed in a second slot 42, the module 33 can be removed from the manifold 2a. (FIGS. 4 and 11.) When a module 33 is thus removed, the remaining modules 33 and the end plates 4c, 4d remain assembled. Thus the construction of the manifold 2a permits rapid replacement of one or more of the valve modules 33 in the field.

Figure 1:
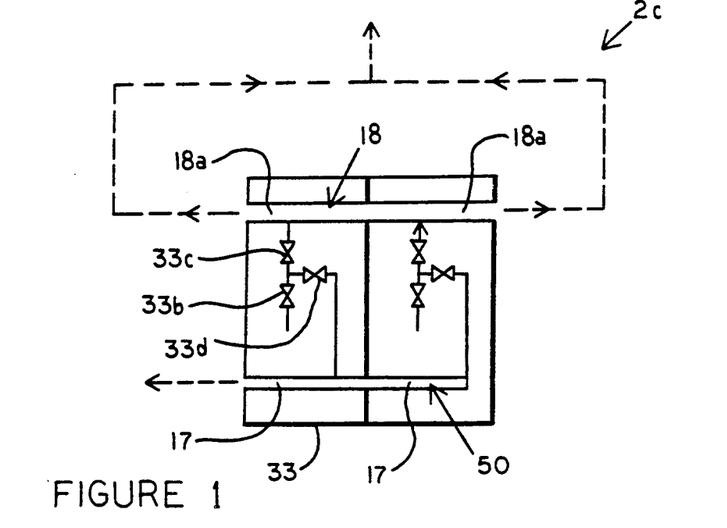
FIG. 1 is a schematic representation of a second embodiment of a stream-selection valve manifold for a process analyzer, made in accordance with the principles of the present invention.

The passageways 18a of the individual valve modules form a common passageway 18 (FIGS. 1 and 3) to an analyzer not shown). This common passageway 18 occupies a very small volume, and is easy to purge out. The passageway 18 is straight and smooth, and has a regular surface, thereby significantly reducing the time required for sample flow (purging) before all residual fluid from a previously-selected sample stream is displaced. In a preferred embodiment, the width of the passageway 18 is from about 0.06" to about 0.08". The volume of each passageway 18a in each valve module 33 is from about 0.06 to about 0.08 cubic centimeters; yet the passageways 18a and 18 are not restrictive of fluid flow. The valve module $C_v$ is 0.05. The passageways 18a are located in very close proximity to the outlet valves 33c. The passageway 30, which connects the outlet valve 33c to the passageway 18a, is preferably from about 0.045" to about 0.055" in length (FIGS. 7, 9, and 10). The passageway 18a purges out cleanly and quickly when serving as a conduit for fluid communication in the manifold 2a. (FIG. 8.) Internal passageways 36 and 47 (FIG. 8) of the end plates 4c and 4d, respectively, are also approximately 0.07" in width. Hence the common passageway 18 servicing the entire manifold 2a has a very small volume and no dead space.

When a valve module 33 is actuated and the block valves 33b, 33c are opened, sample fluid from that module flows into the common passageway 18 and out of both end plates 4c, 4d. (FIGS. 4 and 8.) The two flow paths may either be joined external to the manifold 2a, or they may remain divided, with fluid flowing from one of the end plates to vent or bypass, and fluid flowing from the other end plate routed to an analyzer. This pattern of fluid flow ensures that the entire common passageway 18 is adequately purged, thereby significantly reducing the number of fittings as well as the labor and time required for assembling the valve manifold 2a.

Figure 2:
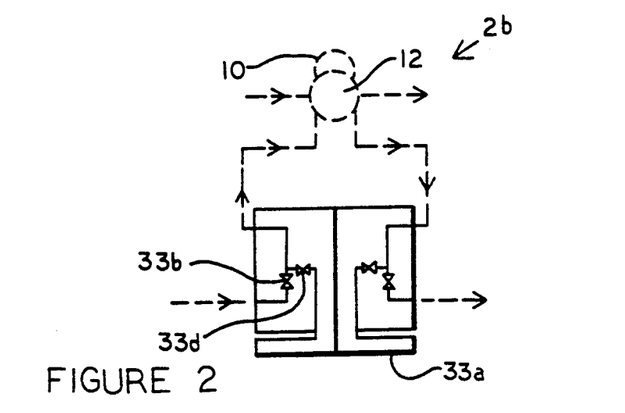
FIG. 2 is a schematic representation of as shutoff and atmospheric reference vent for a process gas chromatograph, made in accordance with the principles of the present invention.
Figure 5:
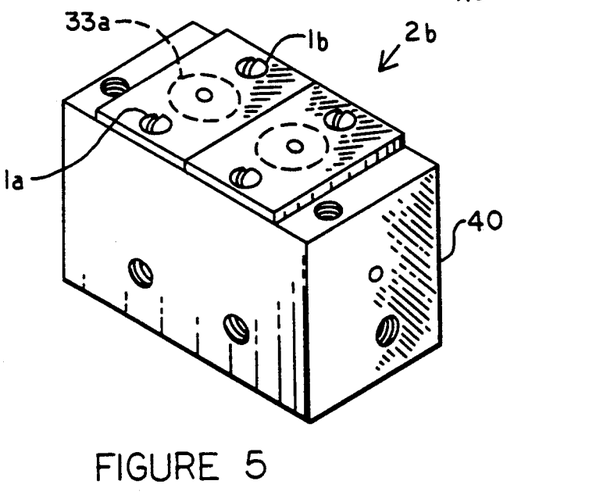
FIG. 5 is an isometric view of the shutoff and atmospheric reference vent shown in FIG. 2.

In a third embodiment (FIGS. 2 and 5), the invention provides a shutoff and atmospheric reference vent 2b for a process gas chromatograph not shown). By removing the O-ring 12b from the poppet 15 (FIGS. 7, 9, and 10) in each of two valve modules 33, and arranging the modified modules 33a as shown, there results a sample shutoff and atmospheric reference vent valve arrangement useful for blocking sample fluid from the sample loop 10 of the injection valve 12 of a gas chromatograph (not shown). The two valve modules 33a are housed in a flow-through modular body 40.

Figure 6:
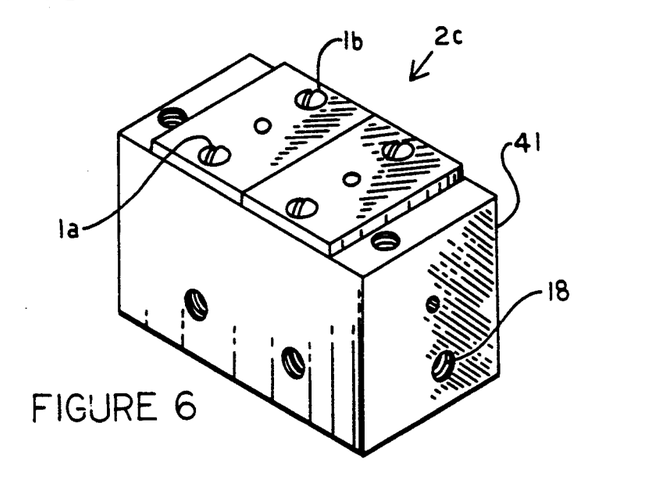
FIG. 6 is an isometric view of the second embodiment of a stream-selection valve manifold for a process analyzer shown schematically in FIG. 1.

In a fourth embodiment, the invention 2c (FIGS. 1 and 6) provides a stream-selection valve manifold comprising two valve modules 33 disposed side-by-side in a flow-through modular body 41, thereby eliminating the need for the end plates 4c, 4d and the mounting brackets 40a, 40b of the manifold 2a (FIGS. 4 and 8).

In a fifth embodiment the present invention provides a single block-and-bleed valve module for selectively controlling fluid flow.

Figure 13:
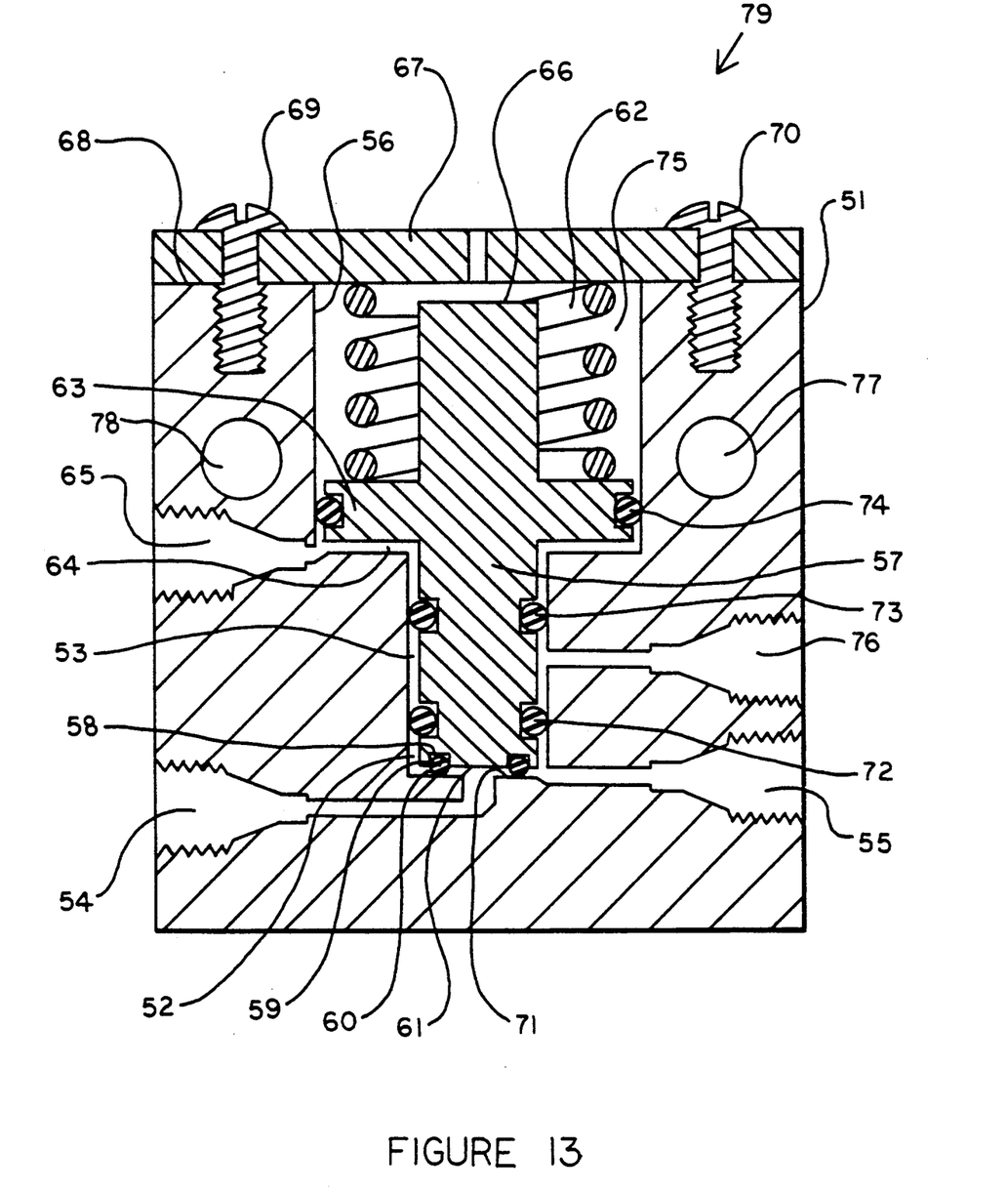
FIG. 13 is a vertical cross-sectional view of a single block-and-bleed valve module, made in accordance with the principles of the present invention.

Reference is made to FIG. 13, which shows that the single block-and-bleed module 79 is comprised of a block valve, a sample fluid compartment 52, a vent compartment 53, and an internal pneumatic actuator, all of which are disposed within a cavity 56 in a body 51. The block Valve is constructed and arranged so that, when closed, fluid communication is blocked between an inlet passageway 54 and the sample fluid compartment 52. In the "open position" of the block valve, an inlet passageway 54, the sample fluid compartment 52, and an outlet passageway 55 are in fluid communication. The outlet passageway 55 and the sample fluid compartment 52 are in fluid communication in both the "open" and "closed" positions of the block valve.

A poppet 57 is axially disposed within the cavity 56. A groove 58 in the lower surface 61 of the poppet 57 retains a first O-ring 59 in axial alignment with the passageway 54. A portion 60 of the O-ring 59 which extends beyond the groove 58, in combination with the lower surface 71 of the compartment 52, forms the block valve which, when the portion 60 of the O-ring 59 is forced against the lower surface 71 of the compartment 52 and in axial alignment with the passageway 54, closes the valve. The passageway 54 provides means for fluid communication from the environment external of the body 51 to the sample-fluid compartment 52. The passageway 55 provides means for fluid communication from the sample-fluid compartment 52 to the environment external of the valve body 51. The function of the passageways 54 and 55 can be reversed without altering the function of the valve module 79.

An actuator piston 63 is formed by an enlargement of the width of the poppet 57 near the longitudinal center of the poppet 57. The poppet 57 is normally maintained in the extreme lower position shown in FIG. 13 by the downward force of a compression return spring 62 applied to the actuator piston 63.

The internal pneumatic actuator comprises the actuator piston 63 and an actuator compartment 64. When an external source of sufficient pneumatic pressure is supplied to the actuator compartment 64 via a passageway 65, an upward force resulting from the pneumatic pressure applied to the lower surface of the actuator piston 63 overcomes the downward force applied by the compression spring 62, and lifts the poppet 57 to its extreme upper position. The upper surface 66 of the poppet 57 contacting cover 67 limits the travel of the poppet 57 in its extreme upper position. The cover 67 is held to the top 68 of the body 51 by screws 69 and 70. The portion 60 of the O-ring 59 contacting the lower surface 71 of the compartment 51 limits the travel of the poppet 57 in its extreme lower position.

The block valve is in a closed mode when the poppet 57 is at its extreme lower position, and in an open mode when the poppet is at its extreme upper position.

The compartment 52 is formed by the annulus between the poppet 57 and the inner surface of the cavity 56, from the lower surface 71 of the cavity 56 to a second O-ring 72.

The vent compartment 53 is formed by the annulus between the poppet 57 and the inner surface of the cavity 56, from the second O-ring 72 to a third O-ring 73.

The actuator compartment 64 is formed by the annulus between the poppet 57 and the inner surface of the cavity 56, from the third O-ring 73 to a fourth O-ring 74. The return spring 62 is housed in a spring compartment 75 formed in the upper portion of the cavity 56 between the fourth O-ring 74 and the lower surface of the cover 67.

A passageway 76 provides fluid communication between the vent compartment 53 and the environment external of the body 51. The end of the passageway 76 terminating at the external surface of the valve body 51 is normally in fluid communication, by tubing or piping means, with an area (not shown) suitable for the safe disposal of sample fluids contained within the sample-fluid compartment 52. Pressure within the passageway 76 and the compartment 53 is normally maintained at a level equal to or lower than than that of the sample-fluid compartment 52, the passageway 54, the passageway 55, and the compartment 64.

The O-rings 72, 73, and 74 provide fluid sealing between the compartments 52, 53, 64, and 75. Should the O-ring 72 fail, resulting in sample fluid from the sample-fluid compartment 52 entering the vent compartment 53, the passageway 76 will conduct this fluid to the safe-disposal area referred to above.

In a similar manner, pneumatic-supply gas entering the vent compartment 53 as a result of breaching the O-ring 73, should that O-ring fail, would also be conducted to the external safe-disposal area in fluid communication with the passageway 76.

These characteristics provide a "bleed" feature which ensures that there will not be fugitive emission of sample fluids or pneumatic gas from the valve module 79 to contaminate the surrounding atmosphere, thereby providing a solution to this problem which has continued to plague the prior art.

Mounting holes 77 and 78 provide convenient means for mounting the Valve module 51.

The flat-face sealing structure of each valve is very tolerant of scratching of and/or irregularities in the sealing means, of abrasive particulates which may be present in the sample fluid, and even of minor structural damage to the sealing means.

While certain specific embodiments and details have been described in order to illustrate the present invention, it will be apparent to those skilled in the art that many modifications can be made therein without departing from the basic concept and scope of the invention.

I claim:

1. A block-and-bleed valve module, comprising
   (a) a first block valve having a first opening, a first passageway, first flat-face sealing means, and a first flat sealing surface;
   (b) a second block valve having a second opening, a second passageway, second flat-face sealing means, and a second flat sealing surface;
   (c) a bleed valve having a third opening, a third passageway, third flat-face sealing means, and a third flat sealing surface; and
   (d) means for closing the first and second block valves and the bleed valve by urging the first, second, and third sealing means against the first, second, and third sealing surfaces, respectively; and for opening the first and second block valves and the bleed valve by breaking contact between the first, second, and third sealing means and the first, second, and third sealing surfaces; the means for closing and opening the first and second block valves and the bleed valve including a valve poppet and an internal pneumatic actuator; the valve poppet having first and second opposite faces, the first and second block valves being disposed on the first face and the bleed valve being disposed on the second face of the poppet, the first and second block valves and the bleed valve being so constructed and arranged that, when the poppet is moved in a first linear direction to a first position, the first and second block valves are closed and the bleed valve is opened, and when the poppet is moved in a second linear and opposing direction to a second position, the first and second block valves are opened and the bleed valve is closed, and the first and second block valves and the bleed valve are open during transition rom the first to the second position and during transition from the second to the first position, thereby necessitating one hundred and eighty degrees out of phase synchronization and an efficient purging of the first and second block valves and the bleed valve.

2. The valve module of claim 1, wherein the pneumatic actuator comprises:
   (e) first biasing means for urging the poppet in a first direction, to seal the openings of the block valves while leaving the bleed valve open, thereby placing the valve module in the first mode; and
   (f) second biasing means for urging the poppet in a second direction, to seal the opening of the bleed valve while opening the first and second block valves, thereby placing the valve module in the second mode;
   the third mode being momentarily formed in transit between the first to the second mode, or in transit between the second to the first mode.

3. The valve module of claim 2, wherein the first biasing means include a compression spring, and the second biasing means include a compressed gas.

4. The valve module of claim 3, further comprising:
   (j) a body having an inlet port, an outlet port, and a vent port for the first block valve, second block valve, and bleed valve, respectively, the body being constructed and arranged to house the pneumatic actuator and the valves in a cavity within the body.

5. The valve module of claim 4, wherein the body cavity comprises:
   (h) a first portion extending form the lower end of the cavity to the lower surface of a seal-plug bottom part;
   (i) a second portion extending from the lower surface of the seal-plug bottom part to the lower surface of a seal-plug top part;
   (j) a third portion extending from the upper surface of the seal-plug top part to the lower surface of the actuator piston; and
   (k) a fourth portion extending from the upper surface of the piston to the lower surface of a cover;
   the block and bleed valves being disposed in the first portion of the cavity, the third passageway in the second portion of the cavity, the second biasing means in the third portion of the cavity, and the first biasing means in the fourth portion of the cavity.

6. The valve module of claim 4, wherein the body cavity:
   (j) has upper and lower ends;
   (k) has a middle portion;
   (l) has a shoulder formed by a reduction of cross-sectional area at the lower end of the cavity;
   (m) includes a seal-plug bottom part disposed on the shoulder;

(n) includes a first O-ring which seals the outer surface of the seal-plug bottom part to the inner surface of the cavity;
(o) includes a seal-plug top art disposed above the seal-plug bottom part;
(p) includes a second O-ring which seals the outer surface of the seal-plug top part to the inner surface of the cavity;
(q) includes retaining means for retaining the seal-plug top part and seal-plug bottom part in a fixed configuration;
(r) includes first and second passageways communicating with outlet and inlet ports, respectively;
(s) includes first and second retaining grooves for the first and second O-rings, respectively;
(t) includes a third O-ring axially disposed around the lower end of the poppet stem;
(u) includes a piston axially disposed and retained on the upper end of the poppet stem, for moving the poppet upward in response to the second biasing means;
(v) includes fourth and fifth O-rings to provide a dynamic seal between the seal-plug top part and the poppet stem; and
(w) includes a sixth O-ring to provide a dynamic seal between the piston and the inside surface of the cavity.

7. The valve module of claim 6, wherein the width and depth of the first and second grooves are from about seventy-five to about ninety-five percent of the width of the first and second O-rings, respectively.

8. The valve module of claim 6, wherein the width of the first and second grooves if from about eighty to about ninety percent of the width of the first and second O-ring, respectively.

9. The valve module of claim 6, wherein the first and second O-rings are made of an elastomer having a hardness of from about sixty-five to about seventy-five durometer units, as measured on a Shore "A" gauge, and the depth of the first and second grooves is from about eighty-seven to about ninety-one percent of the width of the first and second O-rings, respectively.

10. The valve module of claim 2, wherein the first and second biasing means include a compressed gas.

11. A block-and-bleed valve module, comprising:
(a) a first block valve having a first opening, a first passageway, first flat-face sealing means, and a first flat sealing surface;
(b) a second block valve having a second opening, a second passageway, second flat-face sealing means, and a second flat sealing surface;
(c) a bleed valve having a third opening, a third passageway, third flat-face sealing means, and a third flat sealing surface, the bleed valve forming a junction with the first and second block valves and communicating therewith;
the block valves and the bleed valve being so constructed and arranged that: in a first mode, the block valves are closed and the bleed valve is open; in a second mode, the block valves are open and the bleed valve is closed; and in a third mode, all of the valves are open;
(d) means for closing the first and second block valves and the bleed valve by urging the first, second, and third sealing means against the first, second, and third sealing surfaces, respectively; and for opening the first and second block valves and the bleed valve by breaking contact between the first, second, and third sealing means and the first, second, and third sealing surfaces; the means for closing and opening the first and second block valves and the bleed valve including a valve poppet and an internal pneumatic actuator; the pneumatic actuator comprising
(e) first biasing means, including an actuator piston, for urging the poppet in a first direction, to seal the openings of the block valves while leaving the bleed valve open, thereby placing the valve module in the first mode;
(f) second biasing means, including the actuator piston, for urging the poppet in a second direction, to seal the opening of the bleed valve while opening the first and second block valves, thereby placing the valve module in the second mode;
the third mode being momentarily formed in transit between the first to the second mode, or in transit between the second to the first mode; the first biasing means including a compression spring, and the second biasing means including a compressed gas;
(g) a body having a cover, an inlet port, an outlet port, and a vent port of the first block valve, second block valve, and bleed valve, respectively, the body being constructed and arranged to house the pneumatic actuator and the valves in a cavity within the body, the body cavity comprising
(h) a first portion extending form the lower end of the cavity to the lower surface of a seal-plug bottom part;
(i) a second portion extending from the lower surface of the seal-plug bottom part to the lower surface of a seal-plug top part;
(j) a third portion extending from the upper surface of the seal-plug top part to the lower surface of the actuator piston; and
(k) a fourth portion extending from the upper surface of the piston to the lower surface of the cover;
the block and bleed valves being disposed in the first portion of the cavity, the third passageway in the second portion of the cavity, the second biasing means in the third portion of the cavity, and the first biasing means in the fourth portion of the cavity.

12. The valve module of claim 11, wherein first and second portion of a lower surface of a compartment within the first portion of the cavity are the first and second sealing surfaces for the first and second block valves, respectively, and the lower surface of the seal-plug bottom part is the third sealing surface for the bleed valve.

13. The valve module of claim 12, wherein the first and second block valves are formed by first and second O-rings which seal when pressed against the lower surface of the compartment within the first portion of the cavity.

14. The valve module of claim 12, wherein the bleed valve includes an O-ring which seals when pressed against the lower surface of the seal-plug bottom part.

15. A stream-selection valve manifold, comprising:
(a) a first valve module comprising
(a1) a first block valve having a first opening, an inlet first passageway, first flat-face sealing means, and a first flat sealing surface;
(a2) a second block valve having a second opening, an outlet second passageway, second flat-face sealing means, and a second flat sealing surface;

the first and second block valves being so constructed and arranged that both are closed simultaneously or both are open simultaneously;

(a3) a first bleed valve having a third opening, a vent third passageway, third flat-face sealing means, and a third flat sealing surface, the first bleed valve forming a junction with the first and second block valves and communicating therewith;

the first and second block valves and the first bleed valve being so constructed and arranged that: in a first mode, the first and second block valves are closed and the first bleed valve is open; in a second mode, the first and second block valves are open and the bleed valve is closed; and in a third mode, all of the valves are open;

(a4) means for closing the first and second block valves and the first bleed valve by urging the first, second, and third sealing means against the first, second, and third sealing surfaces, respectively; and for opening the first and second block valves and the bleed valve by breaking contact between the first, second, and third sealing means and the first, second, and third sealing surfaces;

(a5) means for urging the first, second, and third sealing means against the first, second, and third flat sealing surfaces to close the first and second block valves and the first bleed valve; and (a6) means for breaking contact between the first, second, and third sealing means and the first, second, and third sealing surfaces to open the first and second block valves and the bleed valve;

(b) a second valve module comprising (b1) a third block valve having a fourth opening, an inlet fourth passageway, forth flat-face sealing means, and a fourth flat sealing surface;

(b2) a forth block valve having a fifth opening, an outlet fifth passageway, fifth flat-face sealing means, and a fifth flat sealing surface;

the third and fourth block valves being so constructed and arranged that both are closed simultaneously or both are open simultaneously;

(b3) a second bleed valve having a sixth opening, a vent sixth passageway, sixth flat-face sealing means, and a sixth flat sealing surface, the second bleed valve forming a junction with the third and fourth block valves and communicating therewith;

the third and fourth block valves and the second bleed valve being so constructed and arranged that: in a first mode, the third and fourth block valves are closed and the second bleed valve is open; in a second mode, the third and fourth block valves are open and the second bleed valve is closed; and in a third mode, all of the valves are open;

(b4) means for closing the third and fourth block valves and the second bleed valve by urging the fourth, fifth, and sixth sealing means against the fourth, fifth, and sixth sealing surfaces, respectively and for opening the valves by breaking contact between the fourth, fifth, and sixth sealing means and the fourth, fifth, and sixth sealing surfaces;

(b5) means for urging the fourth, fifth, and sixth sealing means against the fourth, fifth, and sixth flat sealing surfaces to close the third and fourth block valves and the second bleed valve; and (b6) means for breaking contact between the fourth, fifth, and sixth sealing means and the fourth, fifth, and sixth sealing surfaces to open the third and fourth block valves and the second bleed valve;

(c) means for holding the first and second valve modules in a fixed configuration wherein (d) the first and second valve modules are joined side-by-side;

(e) the second and fifth passageways are aligned to form a common outlet passageway to and through the holding means; and (f) the third and sixth passageways are aligned to form a common vent passageway.

16. The stream-selection manifold of claim 15, further comprising:

(g) a first flow-through modular body for housing the first valve module, the first modular body having a first inlet port, a first outlet port, and a first vent port communicating with the first passageway, second passageway, and third passageway, respectively; and (h) a second flow-through modular body for the second valve module, the second modular body having a second inlet port, a second outlet port, and a second vent port communicating with the fourth passageway, the fifth passageway, and the sixth passageway, respectively.

17. The stream-selection manifold of claim 15, wherein:

(g) the width of the common outlet passageway is from about six/one-hundredth's to about eight-/one-hundredth's of an inch;

(h) the volume of the second and fifth passageways is from about six/one-hundredth's to about eight-/one-hundredth's of a cubic centimeter; and (i) the $C_v$ of the first and second valve assemblies is from about 0.04 to about 0.06.

18. The stream-selection manifold of claim 15, further comprising:

(g) first and second threaded rods, for holding the manifold together;

(h) first, second, third, and fourth slots;

(i) a first pivot point, comprising the first rod disposed in the fist slot, about which the first valve module can be rotated until the third slot is clear of the second threaded rod, after which the first valve module can be removed from the manifold without removing the second valve module, the first rod, or the second rod; and (j) a second pivot point, comprising the second rod disposed in the second slot, about which the second valve module can be rotated until the fourth slot is clear of the second threaded rod, after which the second valve module can be removed from the manifold without removing the first valve module, the first rod, or the second rod.

* * * * *